United States Patent [19]
Peyman

[11] Patent Number: 5,824,073
[45] Date of Patent: Oct. 20, 1998

[54] MACULAR INDENTOR FOR USE IN THE TREATMENT OF SUBRETINAL NEOVASCULAR MEMBRANES

[76] Inventor: Gholam A. Peyman, 2020 Gravier St., Ste. B, New Orleans, La. 70112-2234

[21] Appl. No.: 717,302

[22] Filed: Sep. 20, 1996

Related U.S. Application Data

[63] Continuation-in-part of Ser. No. 617,114, Mar. 18, 1996, Pat. No. 5,743,274.

[51] Int. Cl.⁶ ....................................................... A61F 2/14
[52] U.S. Cl. ................................................. 623/4; 602/74
[58] Field of Search ............................. 623/4, 5; 602/42, 602/53, 61, 63, 74; 606/107, 204.25; 604/7, 8, 9

[56] References Cited

U.S. PATENT DOCUMENTS

| | | | |
|---|---|---|---|
| 4,549,529 | 10/1985 | White | 623/4 |
| 4,902,292 | 2/1990 | Joseph | 623/6 |
| 4,990,150 | 2/1991 | Tsubota et al. | 623/4 |
| 5,180,360 | 1/1993 | Rhame, Jr. | 602/53 |
| 5,284,261 | 2/1994 | Roizenblatt | 606/192 |
| 5,338,291 | 8/1994 | Speckman et al. | 623/4 |
| 5,489,299 | 2/1996 | Schachar | 623/4 |

FOREIGN PATENT DOCUMENTS 2 553 658 A  4/1985  France ........................ 623/4

OTHER PUBLICATIONS

Intravitreal Surgery, Chapter 8 Posterior Segment Techniques, pp. 344–347, Lincoff Temporary Balloon Buckle Roizenblatt J., an abstract presented in ARVO, 1996, p. 1827.

*Primary Examiner*—Michael J. Milano
*Assistant Examiner*—Tram A. Nguyen
*Attorney, Agent, or Firm*—Haverstock, Garrett and Roberts

[57] ABSTRACT

A macular indentor for positioning over a macular area of an eye comprises a strip of material having a pair of opposed ends, the strip having a raised portion for indenting the macular area of the eye. The macular indentor is also inflatable for selectively applying pressure to the macular area of the eye.

10 Claims, 3 Drawing Sheets

MACULAR INDENTOR FOR USE IN THE TREATMENT OF SUBRETINAL NEOVASCULAR MEMBRANES

This application is a continuation-in-part of U.S. Ser. No. 08/617,114, now U.S. Pat. No. 5,743,274, which was filed on Mar. 18, 1996.

BACKGROUND OF THE INVENTION

This invention relates to a macular indentor for use in the treatment of subretinal neovascular membranes, and in particular to a macular indentor which is used to reduce vascular congestion in the treatment of subretinal neovascular membranes.

Age-related macular degeneration (AMD) is the leading cause of visual loss among adults aged 65 years or older in Western countries. Although neovascular AMD accounts for only 10% of all cases, it is responsible for 80% to 90% of legal blindness due to this disease and is the most common cause of choroidal neovascularization (CNV) in this age population. The pathological changes leading to CNV involve the complex of tissues in the choriocapilaris, Bruch's membrane, and the retinal pigment epithelium (RPE) with secondary involvement of the neurosensory retina. Essentially anything that alters the retinal pigment epithelium and Bruch's membrane can cause CNV. A variety of conditions other than AMD have been associated with CNV, including ocular histoplasmosis syndrome (POHS), pathologic myopia, angioid streaks, and idiopathic causes. Most histopathological studies have been performed in eyes with AMD. The histopathological feature common to many eyes that develop CNV is a break in Bruch's membrane. The capillary-like neovascularization originates from choroidal vessels and extends through these breaks. Age-related macular degeneration accounts for the largest group of patients with CNV. Most symptomatic CNV's are subfoveal and demonstrate an extremely poor natural history. Subfoveal neovascularization is defined as lesions lying under the geometric center of the foveal avascular zone (FAZ). Of untreated eyes followed for 2 years in a Macular Photocoagulation Study (MPS), only 5% had a final visual acuity better than 20/100, whereas 88% had a final visual acuity of 20/200 or worse. Laser photocoagulation has been the mainstay of therapy for choroidal neovascularization. Through a series of well-executed randomized, prospective clinical trials, the MPS established the superiority of photocoagulation over observation for CNV in a variety of settings. Specifically, photocoagulation treatment of extrafoveal and juxtafoveal neovascular membranes in AMD and other disorders was found to be beneficial compared to the no treatment group. In order to treat the entire area of CNV, the ophthalmologist has to be able to identify the boundaries of the choroidal neovascular membrane. Therefore, treatment is indicated only when the boundaries of the CNV are well demarcated. Unfortunately, occult or ill-defined new vessels are the most common pattern at presentation for exudative macular lesions in AMD. In one study, visible or classic neovascular membranes involved only 23% of eyes referred for treatment. The MPS recently reported results of photocoagulation for subfoveal neovascular lesions in AMD showed benefit of laser treatment, but the difference between the treatment and observation groups was small and was seen only after two and five years. Also, as the laser energy destroys both the retina and subretinal membrane, there was a precipitous drop in visual acuity associated with treatment. These results underline both the poor natural history of the condition and the limitations of photocoagulation as a treatment modality.

Since the majority of CNV lesions associated with AMD are considered ineligible for laser treatment because of obscured boundaries, size and location, other options have been considered for treatment. One of these options is subretinal neovascular membrane removal using vitrectomy techniques. According to a study by Thomas and colleagues, neovascular membranes in AMD can indeed be removed, but the intrinsic growth patterns of the neovascular complexes limit the visual outcome in most eyes and does not appear to offer significant benefit over observation or laser photocoagulation. In this particular study, of 41 operated eyes, only 5% retained good central visual acuity of 20/40 or better, whereas visual acuity in 88% of the operated eyes were 20/200 or worse. Although the results after removal of choroidal neovascular membranes (CNM) associated with idiopathic and postinflamatory lesions are good, those associated with membranes secondary to angiod streaks and high myopia are similar to those seen in AMD. Clinical evidence and laboratory studies suggest that the integrity of the subfoveal retinal pigment epithelium (RPE) and choriocapillaris is one important factor in determining visual prognosis after submacular surgery. Gass has classified subfoveal membranes in patients with POHS by whether the CNM lies under the RPE (type 1) or between the RPE and the neurosensory retina (type 2). In AMD, the choroidal neovascular membrane is intimately associated with the RPE and the pigment epithelial cells are thus removed at the time of surgery in most patients. Laboratory studies demonstrate that persistent areas of bare, subfoveal RPE will lead to secondary atrophy of the choriocapillaris and outer retina. It is unlikely that refinement of surgical instrumentation will lead to further improvement in visual results in these eyes. Subretinal surgery might help in decreasing the size of the central scotoma at 6 months and 1 year, with remaining vision associated with the development of an eccentric fixation locus.

Interferon alpha-2a has been found to have an antiangiogenesis effect in vitro and in vivo and is used clinically for the treatment of congenital hemangioma lesions. It has been used in the treatment of CNV from exudative AMD with sistemically administered doses of 3.0 to 6.0 million u/m of body surface area every other night for 8 to 12 weeks. The results have been so far disappointing with zero regression of the CNM in fluorescein angiography and a visual acuity less or equal to 20/200 in 10 patients in one series and no improvement of visual acuity with severe sistemic effects in 90% of 20 patients in another series.

Another technique in the treatment of subfoveal CNM which has been proposed by Coscas is the perifoveal and macular scatter photocoagulation. The first treatment modality was considered effective in preservation of visual acuity, but only if baseline acuity was 20/100 or worse, and also for a limited time. In the case of macular scatter photocoagulation, there was no statistical difference in visual acuity between treated and observed eyes.

Other approaches to the treatment of subfoveal choroidal neovascular membranes at an experimental level include vascular targeting with photodynamic occlusion of subretinal vessels, external beam radiotherapy on the macular region, and subretinal endophotocoagulation of choroidal neovascular membranes. Although some of these treatments appear to be promising, they still need further evaluation, testing, and refinement.

The relationship between AMD or chronic systemic hypertension, and disturbances of the choriocapillary bed in AMD has long been a subject of dispute. Histopathological studies have demonstrated consistent changes in the choroidal vascular bed in patients with AMD and it appears that alterations in the choroidal circulation with age are associated with the development of AMD. These changes include sclerosis of the choriocapillaris with thickening of the septa and narrowing of the lumen and replacement of the sinusoidal capillary network by a tubular system. Indeed, a significant association between AMD and systemic hypertension was demonstrated in human patients.

On the basis of the choroidal anatomy and pathophysiological abnormalities that involve the RPE, Bruch's membrane, and choriocapillaries in AMD, it is speculated that these elements become compromised by excessive permeability of the choroidal vessels. This hyperpermeability of the choroidal vessels leads to the formation of abnormal new vessels which pass through a break in Bruch's membrane to invade the subpigment epithelium and subsensory retinal space. By applying external pressure using a posterior buckle from the scleral side, the buckle attempts to decrease choroidal congestion under the macula and reduces vascular leakage thus preventing abnormal vessel proliferation. This procedure will not reverse the degenerative process of the RPE or destroy the neovascular membrane directly, but it is an attempt to stop or reduce the vascular leakage or hemorrhage that will ultimately lead to destruction of the photoreceptors.

As described above, one of the major limiting factors in successful treatment of subretinal neovascular membranes is the inability to reduce or decrease blood flow through the subretinal neovascular membrane. Thus, a device or treatment method which will reduce vascular congestion or decrease blood flow through the subretinal neovascular member would be advantageous. The present invention is therefore based upon the need and great interest to develop methods and constructions which obviate the limitations of currently available modes of therapies. An ideal device would be one in which bleeding could be reduced or neurosensory fluid accumulation could be reduced in the subretinal neovascular membrane. A device which can selectively indent the macular area of the eye to place pressure in the macular area is also an example of an ideal device. Additionally, combining a mechanical decongestion device with a local active agent that can stop vascular proliferation provides the best of both worlds.

SUMMARY OF THE INVENTION

One preferred embodiment of the present invention is a macular indentor for positioning over a macular area of an eye, the indentor comprises a strip of material having a pair of opposed ends, the strip having a raised portion for indenting the macular area of the eye.

In another preferred embodiment of the present invention a macular indentor for positioning over a macular area of an eye for treating a disorder of the eye is disclosed. The macular indentor comprises a tube of material having a pair of opposed ends and a portion of the tube is inflatable to selectively apply pressure to the macular area.

A method of treating a disorder of an eye is disclosed wherein the eye has a macular area and a sclera, the method comprises the steps of positioning over the macular area a strip of material having a pair of opposed ends and suturing at least one of the ends to the sclera.

Accordingly, it is an object of the present invention to provide a macular indentor for applying pressure to the macular area of the eye.

It is another object of the present invention to provide a macular indentor for treating a disorder of the eye which does not impair or damage ocular structures.

Another object of the present invention is to provide a macular indentor for treating a disorder of the eye which is inflatable.

It is a further object of the present invention to provide a macular indentor for treating a disorder of the eye by providing a macular indentor which is used to decrease congestion of the choroid and to decrease blood flow through the subretinal neovascular membrane to decrease bleeding and subretinal fluid accumulation.

A still further object of the present invention is to provide a macular indentor to reduce vascular congestion and to treat subretinal neovascular membranes.

It is an object of the present invention to provide a macular indentor which is of a simple construction and easy to implant in the eye to reduce vascular congestion and to treat subretinal neovascular membranes.

These and other objects and advantages of the present invention will become apparent after considering the following detailed specification in conjunction with the accompanying drawings, wherein:

DETAILED DESCRIPTION OF THE PREFERRED EMBODIMENT

Figure 1:
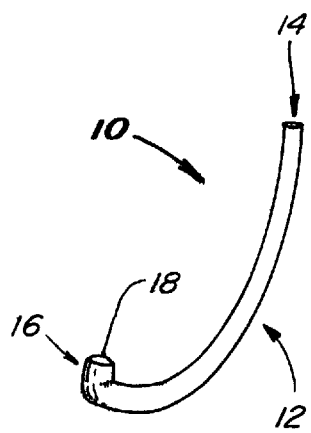
FIG. 1 is a perspective view of a macular indentor constructed according to the present invention.
Figure 2:
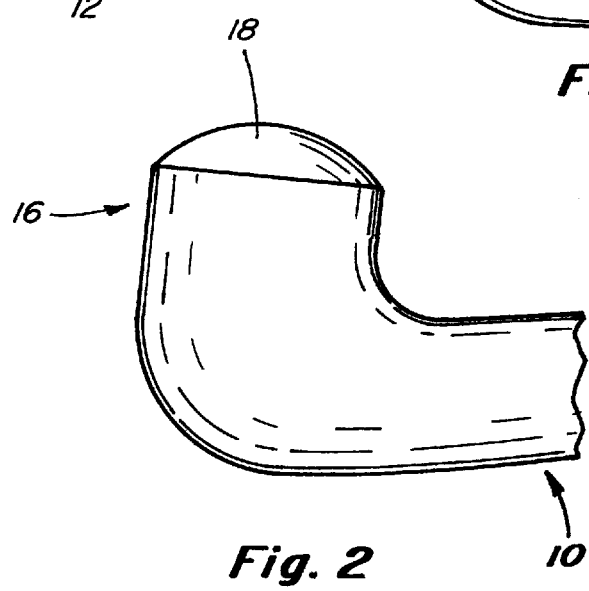
FIG. 2 is an enlarged partial perspective view of the macular indentor shown in FIG. 1.
Figure 3:
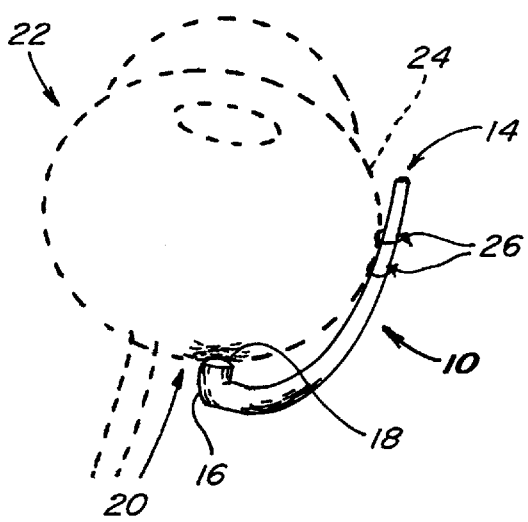
FIG. 3 is a partial perspective view of the macular indentor shown in FIG. 1 with the macular indentor positioned over an eye with the eye shown in phantom.

Referring now to the drawings, wherein like numerals refer to like items, number 10 identifies a preferred embodiment of a macular indentor which is constructed according to the present invention. With reference now to FIGS. 1, 2, and 3, the macular indentor 10 comprises a solid strip or tube of material 12 having a pair of ends, such as opposed ends 14 and 16. The strip 12 is made of a suitable non-toxic material such as silicone, plastic, polymeric plastic, synthetic materials, organic material, or a combination of silicone and plastic. Other examples of synthetic materials are nylon and dacron. Examples of organic materials are duramater, fascia lata, or sclera. The strip 12 has any suitable width and length which is dependent upon the size of an eye to be treated. For example, the width of the indentor 10 may vary in the range of 1 to 5 mm and the length of the indentor 10 may vary in the range of 50 to 100 mm. The indentor 10 further has a raised portion 18 on the end 16. The raised portion 18 is curved or dome shaped. The raised portion 18 is used to indent or apply pressure to a macular area 20 of an eye 22, as best illustrated in FIG. 3. Additionally, the strip 12 at the end 14 may be sutured to the sclera 24 of the eye 22 by use of sutures 26. Furthermore, the indentor 10 may be incorporated with a therapeutic agent for treatment purposes.

Figure 4:
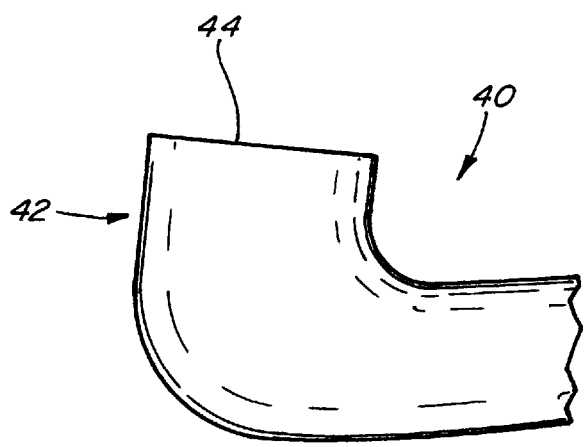
FIG. 4 is a partial perspective view of a further preferred embodiment of a macular indentor constructed according to the present invention.

FIG. 4 depicts another embodiment of a macular indentor 40 which is similar to the macular indentor 10 with the principal difference being the end 16. The macular indentor 40 comprises an end 42 having a raised portion 44 which has a flat surface. The raised portion 44 is used to indent or apply pressure to the macular area of the eye. Additionally, the macular indentor 40 may be sutured to the eye as has been discussed.

Figure 5:
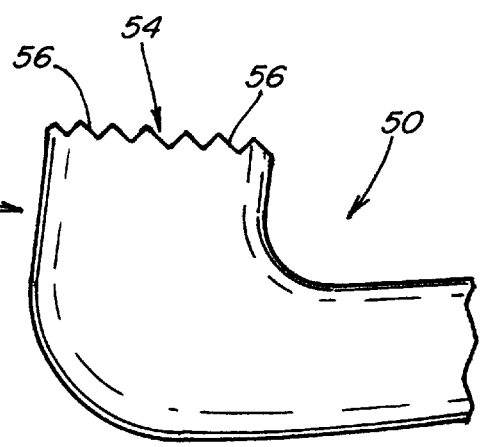
FIG. 5 is a partial perspective view of another embodiment of a macular indentor constructed according to the present invention.

With reference now to FIG. 5, another embodiment of a macular indentor 50 is shown which is similar to the macular indentors 10 and 40, again, with the principal difference being the end 16. The macular indentor 50 comprises an end 52 having a raised portion 54 which has a serrated edge 56. The raised portion 54 is used to indent or supply additional pressure to the macular area of the eye. The serrated edge 56 of the raised portion 54 allows the macular indentor 50 to stay in position once it is placed over the macular area. The macular indentor 50 may also be sutured to the eye.

Figure 7:
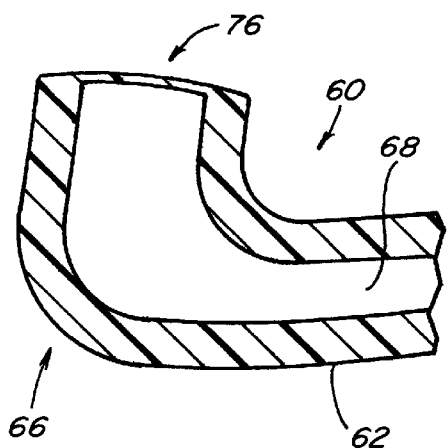
FIG. 7 is a partial cross-sectional view of the macular indentor shown in FIG. 6 shown in a deflated state.
Figure 6:
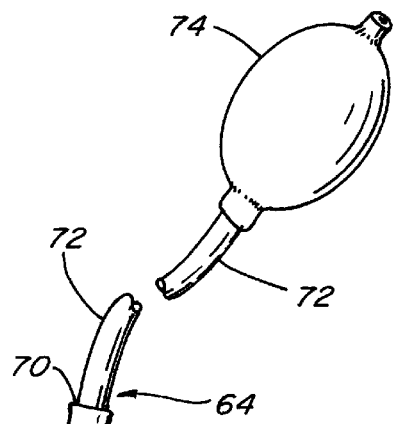
FIG. 6 is a cross-sectional view of another embodiment of a macular indentor shown in an inflated state.
Figure 6:
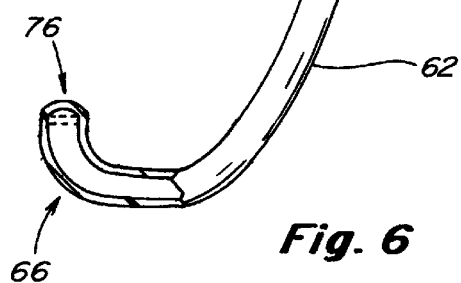

FIG. 6 illustrates another embodiment of a macular indentor 60 constructed according to the present invention. The macular indentor 60 comprises a hollow strip or tube of material 62 having a pair of ends, such as opposed ends 64 and 66. The strip 62 is made of a suitable non-toxic material such as silicone, plastic, polymeric plastic, synthetic materials, organic material, or a combination of silicone and plastic. Other examples of synthetic materials are nylon and dacron. The strip 62 has any suitable width and length which is dependent upon the size of an eye to be treated. For example, the width of the indentor 60 may vary in the range of 1 to 10 mm and the length of the indentor 60 may vary in the range of 50 to 100 mm. The strip 62 has a hollow interior 68 and the end 64 has an opening 70 which allows a tubing 72 to be inserted therein. The tubing 72 is connected to a reservoir 74 for holding a substance or a solution, such as saline, a liquid polymer such as silicone, or air. The reservoir 74 also includes an intricate valve (not shown) which prevents the solution from returning to the reservoir 74 once the solution has been sent into the tubing 72. The indentor 60 further has a raised portion 76 on the end 66. The raised portion 76 is inflatable and is shown in an inflated state in FIG. 6 and a deflated state in FIG. 7. The raised portion 76 is used to selectively indent or apply pressure to a macular area of an eye by placing the end 66 over the macular area and then sending solution from the reservoir 74 into the strip 62 to inflate the raised portion 76. Once the raised portion 76 has been inflated to the desired amount the tubing 72 is removed and the opening 70 is sealed. The macular indentor 60 is used to selectively indent the macular area.

Figure 8:
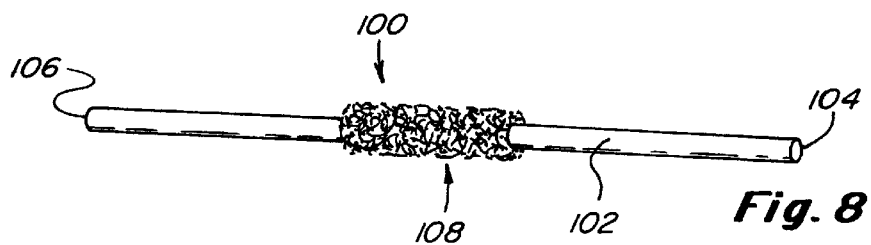
FIG. 8 is a perspective view of still another embodiment of a macular indentor constructed according to the present invention.

Another embodiment of a macular indentor 100 is shown in FIG. 8. The macular indentor 100 comprises a solid strip of material 102 having a pair of opposed ends 104 and 106. The strip 102 is made of a suitable non-toxic material such as silicone and the strip 102 has any suitable diameter and length which is dependent upon the size of an eye to be treated. For example, the diameter of the indentor may be 1–4 mm and the length of the indentor 100 may vary in the range of 50 to 100 mm. The indentor 100 further has a sponge 108, such as a silicone sponge, centrally located along the length of the strip 102. The sponge 108 is tubular in shape and has a diameter of about 2–10 mm. The sponge 108 is used to indent or apply pressure to the macular area of the eye.

Figure 9:
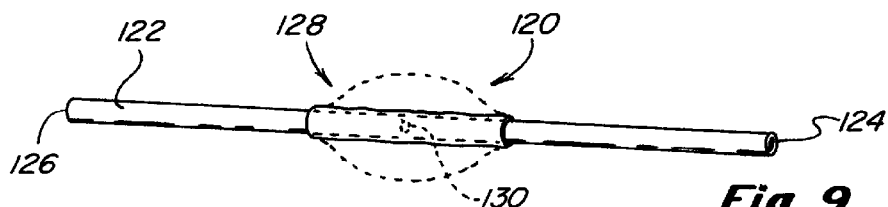
FIG. 9 is a perspective view of another embodiment of a macular indentor constructed according to the teachings of the present invention.

Referring now to FIG. 9, another embodiment of a macular indentor 120 is illustrated which comprises a strip or tubing 122 of material, such as a non-toxic material such as silicone, plastic, polymeric plastic, synthetic materials, organic material, or a combination of silicone and plastic. The tubing 122 has a pair of opposed ends 124 and 126 and a centrally positioned inflatable portion 128 which has an opening 130. The opening 130 may have inserted therein a tubing (not shown) which is connected to a reservoir (not shown). The reservoir may contain a substance or a solution such as air, saline, or a gas which is used to inflate the inflatable portion 128. The inflatable portion 128 is inflated once it has been positioned over the macular area of the eye. The inflatable portion 128 is used to selectively indent or apply pressure to the macular area.

Figure 10:
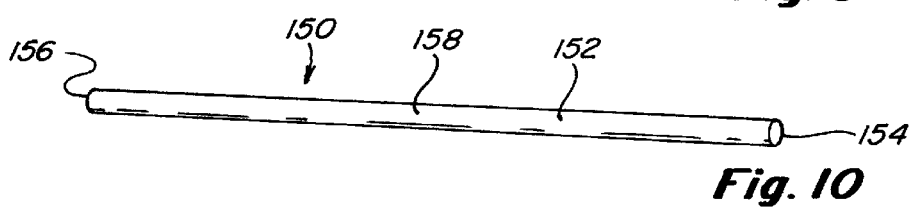
FIG. 10 is a perspective view of yet another embodiment of a macular indentor constructed according to the present invention and shown in a deflated state.
Figure 11:
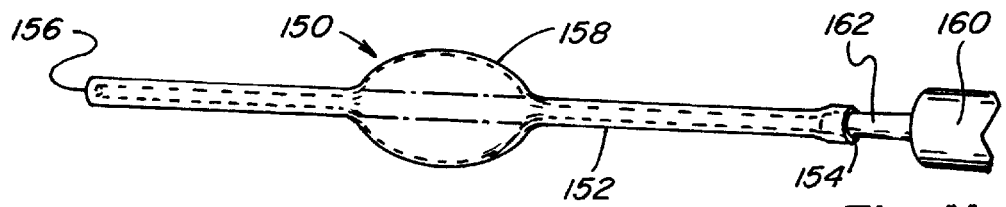
FIG. 11 is a perspective view of the macular indentor shown in FIG. 10 shown in an inflated state.

FIG. 10 shows a macular indentor 150 which comprises a hollow strip or tube 152 having a pair of opposed ends 154 and 156. A central portion 158 is designed to be inflatable. The strip 152 is made of any suitable non-toxic material such as silicone, plastic, polymeric plastic, synthetic materials, organic material, or a combination of silicone and plastic. The strip 152 has a diameter in the range of 0.5–10 mm and a length of about 30–110 mm. FIG. 11 illustrates a syringe 160 having a needle 162 inserted into the end 154 being used to introduce a solution, such as saline or a gas such as air, into the macular indentor 150 to inflate the central portion 158. The central portion 158, once inflated, selectively indents the macular area of the eye. The degree of indentation is controlled by the amount of solution or gas used to inflate the central portion 158 of the indentor 150.

Figure 12:
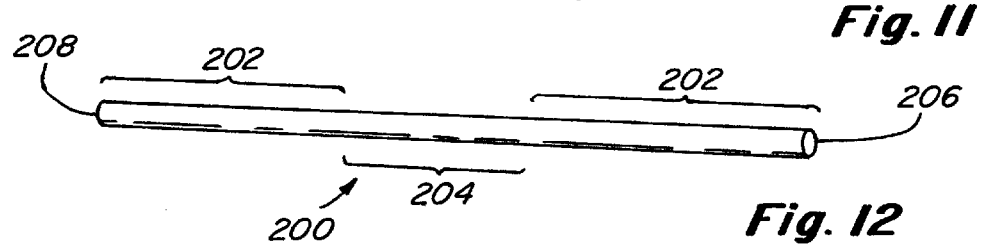
FIG. 12 is a perspective view of another macular indentor constructed according to the present invention.
Figure 13:
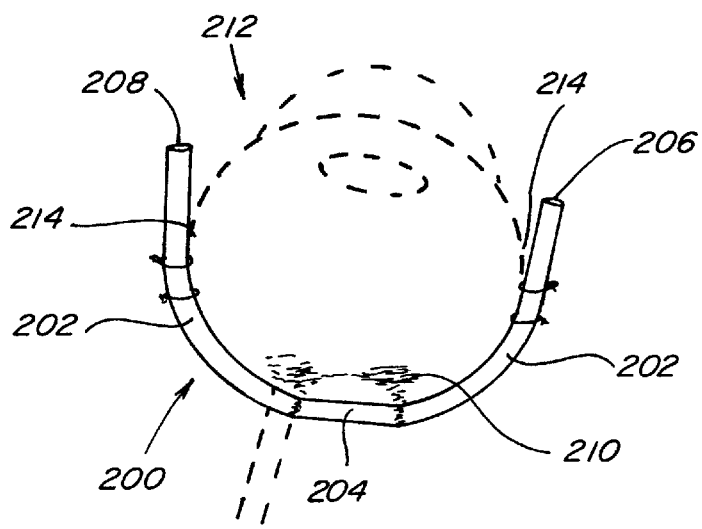
FIG. 13 is a perspective view of the macular indentor shown in FIG. 12 positioned over an eye.

With reference now to FIG. 12, a macular indentor 200 is shown which comprises a hollow tube 202 having inserted therein a solid rod portion 204 which is centrally positioned within the tube 202. The rod portion 204 may be constructed of polymethylmetacrylate or other hard or semi-hard polymer, glass, or metal. The rod portion 204 has a diameter in the range of 0.2–10 mm and a length in the range of 1–8 mm with the preferred length being 4–6 mm. The tube 202 has a diameter of about 0.5–10 mm and a length in the range of 30–110 mm. The indentor 200 also has a pair of opposed ends 206 and 208. FIG. 13 illustrates the indentor 200 positioned over the macular area 210 of the eye 212. The rod portion 204 flattens the macular area 210 and the ends 206 and 208 can be sutured to the sclera 214 of the eye 212.

Figure 14:
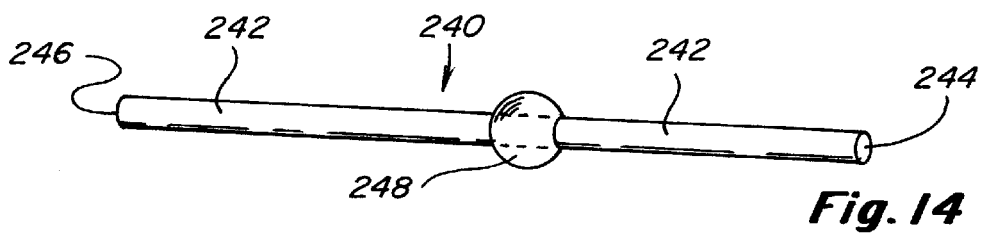
FIG. 14 is a perspective view of still another embodiment of a macular indentor constructed according to the present invention.

Referring now to FIG. 14, a macular indentor 240 is depicted which comprises a band 242 having a pair of opposed ends 244 and 246. The band 242 may be made of any suitable non-toxic material such as silicone. The band 242 further includes a bead 248 positioned at the center of the band 242. The bead 248 may be made of any suitable non-toxic material such as silicone or methacrylate. The band 242 may have a width of about 2.5 mm and a thickness of about 1 mm. The bead 248 has a diameter of about 3–8 mm. The bead 248 is placed over the macular area of the eye to indent the macular area.

Figure 15:
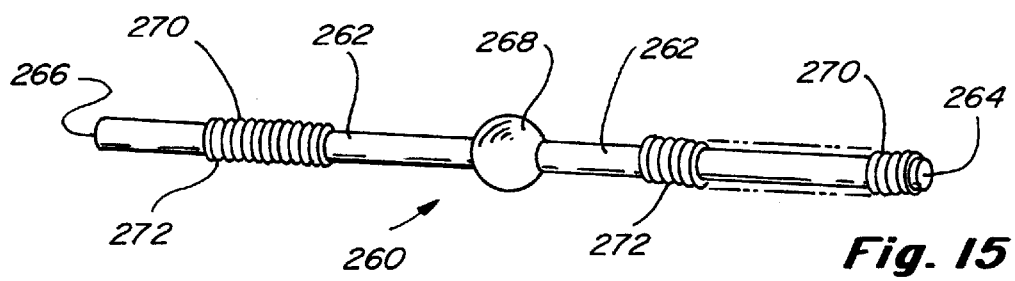
FIG. 15 is a perspective view of another preferred embodiment of a macular indentor constructed according to the present invention.

FIG. 15 illustrates a macular indentor 260 which comprises a band 262 having a pair of opposed ends 264 and 266. A bead 268 is positioned at the center of the band 262. The band 262 further includes serrated edges 270 and 272. The serrated edges 270 and 272 may extend along the entire length of the band 262 or partially along the length of the band 252. The band 262 may be, for example, 120 mm long and about 2 mm wide. The bead 268 may be about 7–8 mm wide. The bead 268 is placed over the macular area of the eye and the serrated edges 270 and 272 hold the sutures and prevent slippage of the band 262 when the band 262 is placed around the eye. Although the serrated edges 270 and 272 are shown with reference to the macular indentor 260, the other macular indentors previously discussed may also include serrated edges.

Patients who may be suitable for a macular indentor may be selected using the following eligibility criteria: (1) pre-operative best corrected Snellen visual acuity of 20/400 or better (2.0 according to the modified Bailey-Lovie chart), as determined by manifest refraction by an independent observer; (2) absence of other eye disease that could significantly limit visual acuity; (3) clinical evidence of a subfoveal or juxtafoveal CNM, including the presence of a neurosensory retinal detachment, intraretinal lipid and/or hemorrhage, and/or presence or a green or gray subretinal elevation consistent with a neovascular membrane; (4) angiographic evidence of a subfoveal or juxtafoveal CNM on fluorescein angiography performed no more than 72 hours prior to surgery, and showing ill-defined or occult characteristics, or being too large in size to be amenable to photocoagulation according to the MPS parameters; and (5) patients denying the alternatives of laser photocoagulation or observation.

From all that has been said, it will be clear that there has thus been shown and described herein a macular indentor and method of using the macular indentor which fulfills the various objects and advantages sought therefor. It will be apparent to those skilled in the art, however, that many changes, modifications, variations, and other uses and applications of the subject macular indentor and method of using the macular indentor are possible and contemplated. All changes, modifications, variations, and other uses and applications which do not depart from the spirit and scope of the invention are deemed to be covered by the invention, which is limited only by the claims which follow.

What is claimed is:

1. A macular indenter for positioning over a macular area of an eye, the indenter comprising a generally J-shaped tubular strip of biocompatible material having a pair of opposed ends and a diameter, the strip having a raised portion at one end of the J-shaped strip for indenting the macular area of the eye, the raised portion closes the one end of the tubular strip and has a diameter which is not greater than the diameter of the J-shaped strip.

2. The macular indentor of claim 1 wherein the raised portion has a domed shape which applies pressure on the macular area.

3. The macular indentor of claim 1 wherein the raised portion has a flat surface which applies pressure on the macular area.

4. The macular indentor of claim 1 wherein the raised portion has a serrated surface which applies pressure on the macular area.

5. The macular indentor of claim 1 wherein the strip is hollow and the raised portion is inflatable to selectively apply pressure to the macular area.

6. The macular indentor of claim 1 wherein the eye includes a sclera and the end opposite the raised portion is sutured to the sclera.

7. A method of treating a disorder of an eye, the eye having a macular area and a sclera, the method comprising the steps of positioning over the macular area a macular indentor comprising a generally J-shaped tubular strip of biocompatible material having a pair of opposed ends and a diameter, the strip having a raised portion at one end of the J-shaped strip for indenting the macular area of the eye, the raised portion closes the one end of the tubular strip and has a diameter which is not greater than the diameter of the J-shaped strip, and suturing at least one of the ends to the sclera.

8. The method of claim 7 wherein the strip further comprises a raised portion and the method further comprises the step of positioning the raised portion over the macular area to apply pressure to the macular area.

9. The method of claim 8 wherein the raised portion is inflatable and the method further comprises the step of inflating the raised portion once the raised portion is positioned over the macular area.

10. The method of claim 7 wherein the strip has serrated edges and the method further comprises the step of positioning the serrated edges over the sclera.

* * * * *